(12) United States Patent
Pan

(10) Patent No.: US 12,414,817 B2
(45) Date of Patent: Sep. 16, 2025

(54) PORTABLE DEPILATION INSTRUMENT

(71) Applicant: Shenzhen Ulike Smart Electronics Co., Ltd., Shenzhen (CN)

(72) Inventor: Yuping Pan, Shenzhen (CN)

(73) Assignee: SHENZHEN Ulike SMART ELECTRONICS CO. LTD., Shenzhen (CN)

( * ) Notice: Subject to any disclaimer, the term of this patent is extended or adjusted under 35 U.S.C. 154(b) by 523 days.

(21) Appl. No.: 17/597,476

(22) PCT Filed: Nov. 23, 2019

(86) PCT No.: PCT/CN2019/120457
§ 371 (c)(1),
(2) Date: Jan. 7, 2022

(87) PCT Pub. No.: WO2021/003950
PCT Pub. Date: Jan. 14, 2021

(65) Prior Publication Data
US 2022/0192745 A1    Jun. 23, 2022

(30) Foreign Application Priority Data

Jul. 7, 2019    (CN) .................. 201921052794.0
Sep. 4, 2019   (CN) .................. 201921467936.X
Nov. 18, 2019  (CN) .................. 201921999189.4

(51) Int. Cl.
*A61B 18/18*    (2006.01)
*A61B 18/00*    (2006.01)

(52) U.S. Cl.
CPC .... *A61B 18/18* (2013.01); *A61B 2018/00017* (2013.01); *A61B 2018/00476* (2013.01)

(58) Field of Classification Search
CPC .......... A61B 18/18; A61B 2018/00017; A61B 2018/00476; A61B 18/203;
(Continued)

(56) References Cited

U.S. PATENT DOCUMENTS

| 6,416,521 | B1 | 7/2002 | Waldner et al. |
| 2005/0177139 | A1 | 8/2005 | Yamazaki et al. |
| 2012/0165682 | A1 | 6/2012 | Keeney et al. |

FOREIGN PATENT DOCUMENTS

| CN | 2490631 Y | 5/2002 |
| CN | 2928026 Y | 8/2007 |

(Continued)

*Primary Examiner* — Scott M. Getzow

(57) ABSTRACT

A portable depilation instrument includes a shell, and a depilation mechanism and a heat dissipation mechanism inside the shell. The shell is provided with at least two outlets and one inlet, the shell introduces an external cooling medium from the inlet, the heat dissipation mechanism includes a heat conductive component, the depilation mechanism includes a refrigeration element and an emitter, the heat conductive component isolates the refrigeration element from the emitter in two mutually sealed channels, namely, a first channel and a second channel, the first channel and the second channel are respectively in communication with two outlets, and one of the outlets allows the first channel or the second channel to pass through inside of the entire shell from one end to the other end. Due to complete isolation and a push force, air can be discharged only from a respective corresponding outlet after a heat exchange.

20 Claims, 19 Drawing Sheets

(58) Field of Classification Search
CPC ........... A61B 2017/00026; A61B 2018/00047;
A61B 2018/00589; A61B 2018/00702;
A61B 2018/00708; A61B 2018/0091;
A61B 2018/1807; A61B 2018/2023;
A61B 2018/20553; A61B 18/00; A61B
2018/00005; A61B 2018/00595; A45D
26/00; A61F 7/007; A61F 2007/0052;
A61F 2007/0075; A61F 2007/0288; A61N
5/0617; A61N 2005/005; A61N 2005/007;
A61N 2005/0644
See application file for complete search history.

(56) References Cited

FOREIGN PATENT DOCUMENTS

| | | | |
|---|---|---|---|
| CN | 201226633 | Y | 4/2009 |
| CN | 101764510 | A | 6/2010 |
| CN | 101848627 | A | 9/2010 |
| CN | 102271478 | A | 12/2011 |
| CN | 102480901 | A | 5/2012 |
| CN | 202776542 | U | 3/2013 |
| CN | 103379794 | A | 10/2013 |
| CN | 103796487 | A | 5/2014 |
| CN | 203970544 | U | 12/2014 |
| CN | 203970545 | U | 12/2014 |
| CN | 104582405 | A | 4/2015 |
| CN | 205698924 | U | 11/2016 |
| CN | 206063571 | U | 4/2017 |
| CN | 207284010 | U | 1/2018 |
| CN | 207164447 | U | 3/2018 |
| CN | 108056816 | A | 5/2018 |
| CN | 207679871 | U | 8/2018 |
| CN | 207804371 | U | 9/2018 |
| CN | 208114942 | U | 11/2018 |
| CN | 208426208 | U | 1/2019 |
| CN | 109328487 | A | 2/2019 |
| CN | 208677571 | U | 4/2019 |
| CN | 208710053 | U | 4/2019 |
| CN | 209464502 | U | 10/2019 |
| CN | 209572304 | U | 11/2019 |
| CN | 113907872 | A | 1/2022 |
| JP | 2009508546 | A | 3/2009 |
| WO | 2021003950 | A1 | 1/2021 |
| WO | 2021027261 | A1 | 2/2021 |

PORTABLE DEPILATION INSTRUMENT

CROSS REFERENCE TO THE RELATED APPLICATIONS

This application is the national phase entry of International Application No. PCT/CN2019/120457, filed on Nov. 23, 2019, which is based upon and claims priority to Chinese Patent Applications No. 201921052794.0, filed on Jul. 7, 2019, No. 201921467936.X, filed on Sep. 4, 2019, and No. 201921999189.4, filed on Nov. 18, 2019, the entire contents of which are incorporated herein by reference.

TECHNICAL FIELD

The present invention relates to the field of depilation and beauty, and specifically, to a portable depilation instrument.

BACKGROUND

A light depilation technology is a non-invasive modern depilation technology, in which unwanted hair can be safely, quickly, and efficiently removed from a body. Specifically, light depilation is based on a theory of selective photothermolysis, in which a specific wavelength of light is allowed to penetrate epidermis without damaging epidermal hair follicles, and melanin in a hair shaft selectively absorbs light energy, so that the hair follicles are coagulated and necrotic during heating, to effectively slow down growth, thereby implementing depilation.

However, it is well known that all light generates a lot of heat during use, which brings a burning pain to skin, especially a household portable depilation instrument. To help users hold and use, all the portable depilation instruments are designed relatively small, and therefore, it is easier to form heat accumulation. In this case, if heat dissipation and temperature reduction cannot be implemented in time, a relatively strong pain and a redness and swollen phenomenon are brought to the users, and even a security problem is caused.

Therefore, in the prior art, to reduce heat generated when the portable depilation instrument performs depilation, a sealing member is disposed in a heat dissipation structure, and an opening is provided on the sealing member and is in communication with outside, to match a heat dissipation fin to independently form a channel for a heating member that needs to be cooled to perform heat dissipation, thereby effectively improving the effect of heat dissipation and temperature reduction. However, the portable depilation instrument has more than one element that generates heat, and generally, internal circuits and other elements also generate heat. Consequently, how to make all the elements that generate heat dissipate the heat under a same power, and how to improve the cooling effect and maximize the efficiency are problems to be resolved currently.

SUMMARY

To resolve a problem of incomplete temperature reduction of an existing portable depilation instrument, the present invention provides a portable depilation instrument.

To resolve the foregoing technical problem, the present invention provides a technical solution as follows: A portable depilation instrument, including a shell, and a depilation mechanism and a heat dissipation mechanism inside the shell, where the shell is provided with at least two outlets and one inlet; the heat dissipation mechanism includes a heat conductive component; the inlet is separately in communication with different outlets, to form at least two channels; each of the channels is provided with an element that generates heat; and after being introduced from the inlet, under guidance of the heat conductive component, an external cooling medium separately passes through different channels and is then discharged from a corresponding outlet, and in this process, the external cooling medium brings heat of the separately passing region out of the shell.

A portable depilation instrument includes a light-emitting body and the foregoing portable depilation instrument.

Figure 1:
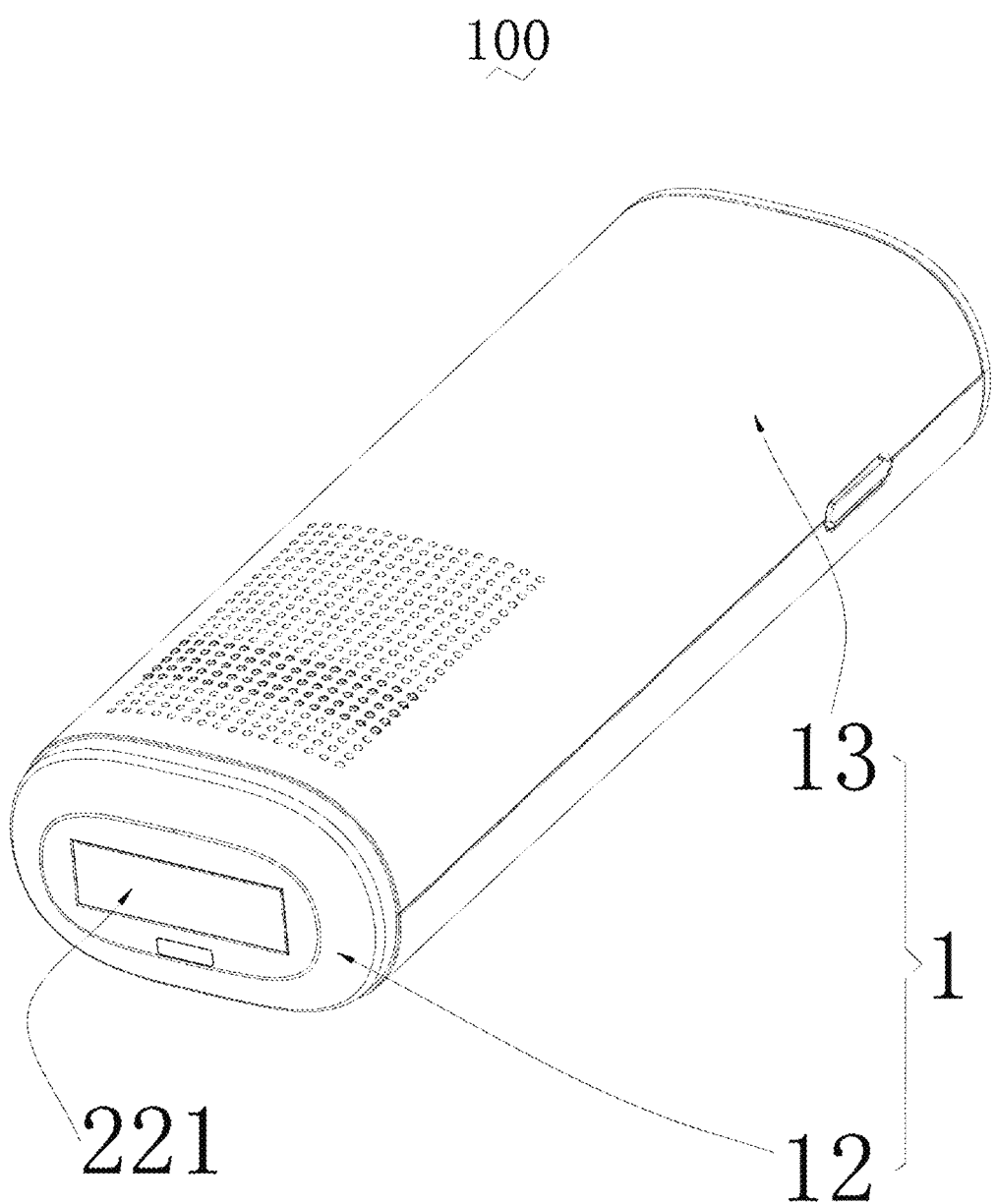
FIG. 1 is a schematic structural diagram of a portable depilation instrument according to a first embodiment of the present invention.

Description of reference numerals: 100. portable depilation instrument;
1. shell; 101. upper shell; 102. lower shell;
11. inlet; 12. head portion; 13. holding portion; 14. second outlet; 15. first outlet; 16. third outlet; 1601. first groove; 1602. second groove; 1603. exhaust structure;
2. depilation apparatus; 21. heat dissipation mechanism; 211. fan; 2111. fan air inlet; 2112. fan air outlet; 2113. heat conductive element; 2114. first heat dissipation fin;
212. heat conductive component; 2121. first vent; 2122. second vent; 2123. second heat dissipation fin; 2124. third vent;
22. depilation mechanism; 221. cold compress portion; 222. emitter; 223. refrigeration element; 2231. heating surface; 2232. refrigeration surface; 224. skin detection portion; 225. reflecting plate; 226. insulating plate;
3. circuit apparatus; and 4. power supply apparatus.

DETAILED DESCRIPTION OF THE EMBODIMENTS

To make the objectives, technical solutions, and advantages of the present invention clearer and more comprehensible, the following further describes the present invention in detail with reference to the accompanying drawings and embodiments. It should be understood that specific embodiments described herein are only intended to explain the present invention, but are not intended to limit the present invention.

Embodiment 1

Referring to FIG. 1, the present invention provides a portable depilation instrument 100, configured to remove unwanted hair from a human body, and including a shell 1 and a cold compress portion 221 having a light-transmitting and cold compress effect. A user may tightly attach the cold compress portion 221 to a human skin surface, the portable depilation instrument 100 emits light, and the light passes through the cold compress portion 221 and penetrates the skin surface to reach a root of a hair follicle, so that the hair follicle is coagulated and necrotic, to remove hair.

The shell 1 mainly plays a role of protecting internal elements, and an overall shape of the shell is not limited, may be U-shaped, T-shaped, shuttle-shaped, or long strip-shaped, or is optionally long striped cylindrical.

The shell 1 includes a holding portion 13 and a head portion 12, the head portion 12 is at one end facing human skin, and the holding portion 13 is parallel with the head portion 12. After the head portion 12 is fixedly connected to the holding portion 13, an accommodating space is formed inside, and the cold compress portion 221 is exposed in the accommodating space from the head portion 12, to be used as a carrier for emitting light and contacting the human skin. The holding portion 13 is used for holding the portable depilation instrument 100, to facilitate operations of the user.

Figure 2:
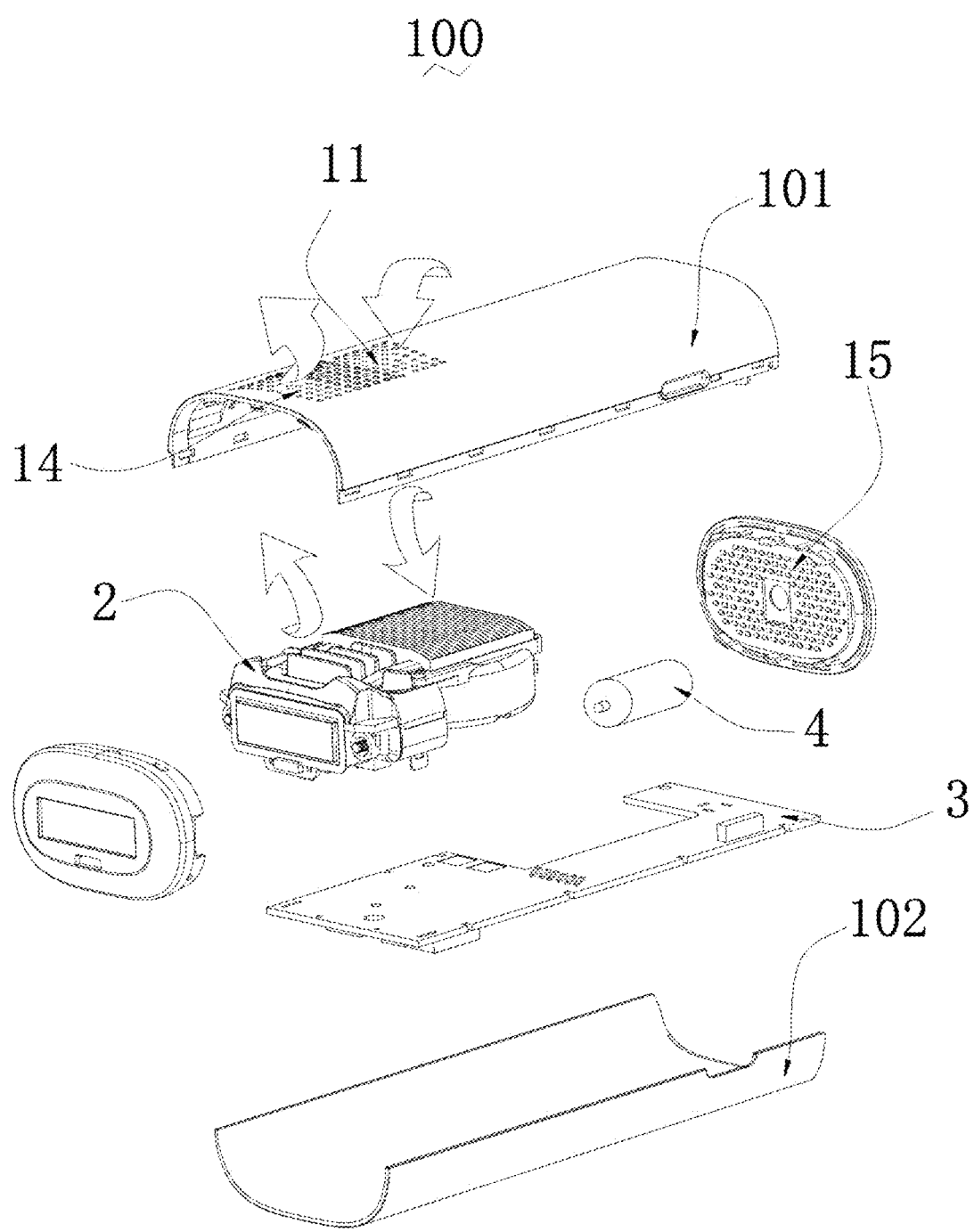
FIG. 2 is a schematic exploded view of the portable depilation instrument according to the first embodiment of the present invention.

Referring to FIG. 2, the shell 1 includes an upper shell 101 and a lower shell 102, may be formed by assembling the upper shell 101 and the lower shell 102 through screw connection or clamping connection, or may be formed through integral processing, or is optionally formed through assembly in a clamping manner, to facilitate disassembly and assembly.

A depilation apparatus 2, a circuit apparatus 3, and a power supply apparatus 4 are included inside the accommodating space of the shell 1. The depilation apparatus 2, the circuit apparatus 3, and the power supply apparatus 4 are all sequentially electrically connected. The power supply apparatus 4 may provide electric energy to the depilation apparatus 2, so that the depilation apparatus can be used without plugging in an external circuit, or can be used by directly using an external power source, such as a dry battery or an energy storage battery. Therefore, the depilation apparatus is convenient to store and carry, and can be used outside. The circuit apparatus 3 may be externally connected to an external circuit to charge the power supply apparatus 4 and control the entire portable depilation instrument 100 on/off, power regulation, and temperature protection.

A person skilled in the art may understand that, during working, all elements in the depilation apparatus 2, the circuit apparatus 3, and the power supply apparatus 4 generate heat.

In daily production, some control elements (not shown in the figure) in the circuit apparatus 3 are generally disposed on a surface of the shell 1, to form a switch, a screen, and an operation panel. The user may control the entire portable depilation instrument 100 through manipulation, to adjust the on/off of the portable depilation instrument 100 and control levels.

The depilation apparatus 2 is disposed at one end near the head portion 12 of the shell 1, and may be fixedly clamped inside the accommodating space of the shell 1. An inlet 11 and a second outlet 14 corresponding to a region of the depilation apparatus 2 are disposed on one side of the shell 1, that is, the upper shell 101 or the lower shell 102. It may be understood that, both the inlet 11 and the second outlet 14 are disposed on a same side of the shell 1, and are closely arranged together. This design is to save a space of the shell 1, so that the shell 1 can be relatively shorter, and is compact and precise, and the inlet 11 and the second outlet 14 are designed together to shorten an air circulation distance of air, to implement rapid air circulation, so that the heat dissipation efficiency is higher.

Further, the first outlet 15 is disposed at an end portion of the shell 1, that is, one end of the shell 1 away from the head portion 12. The reason why the first outlet 15 is remotely disposed is to increase a distance through which the air flows, so that a cooling range is wider.

It may be understood that, during normal production, both the circuit apparatus 3 and the power supply apparatus 4 are disposed inside the shell, and are optionally disposed inside the holding portion 13. In this embodiment, both the circuit apparatus and the power supply apparatus are disposed on a back side of the depilation apparatus 2, that is, one side of the depilation apparatus 2 away from the human skin. By using this design, a range of the air involved is expanded, to achieve an overall cooling effect inside the shell.

Figure 3:
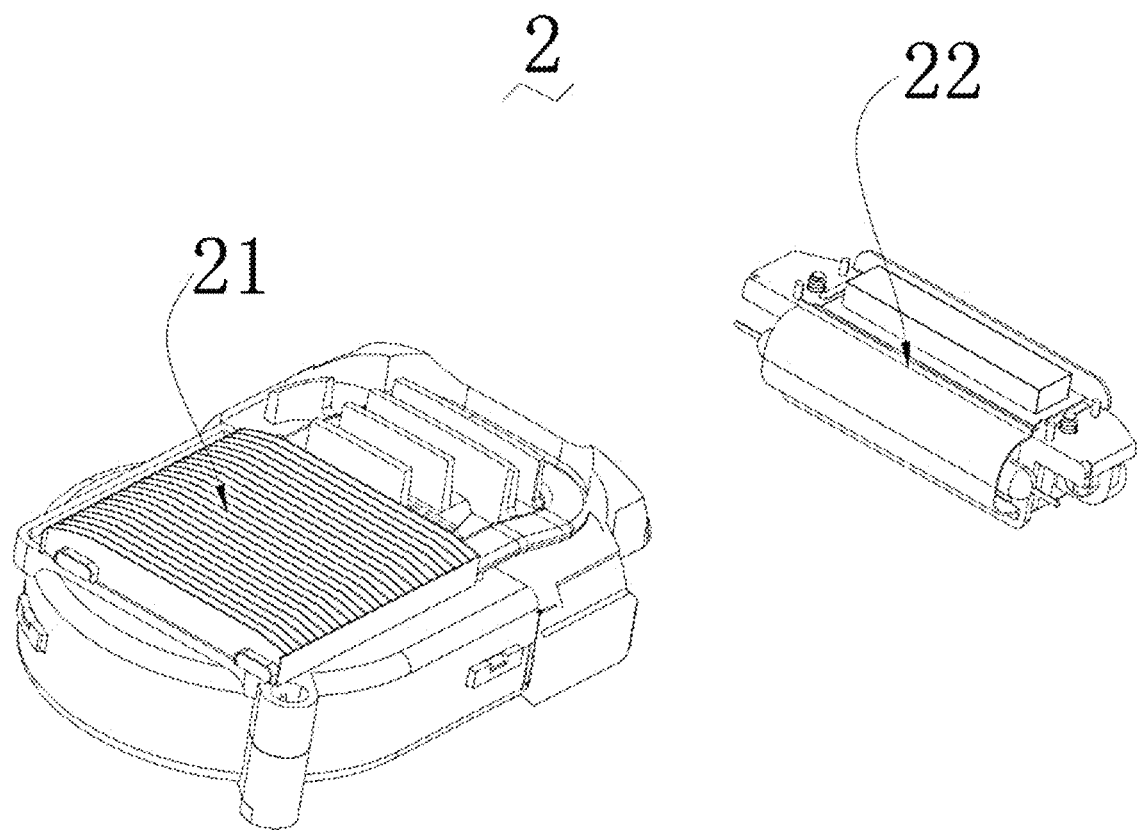
FIG. 3 is a first partial exploded view of a depilation apparatus in the portable depilation instrument according to the first embodiment of the present invention.

Referring to FIG. 3, the depilation apparatus 2 includes a heat dissipation mechanism 21 and a depilation mechanism 22. The depilation mechanism 22 emits light to remove hair from the human body, and is mainly in contact with the human skin. The heat dissipation mechanism 21 is used for reducing a temperature, so that the human body does not have a burning sensation under the light; and the heat dissipation mechanism 21 and the depilation mechanism 22 may be connected through clamping connection or screw connection, or are optionally connected through screw connection, so that fixation is more stable.

Figure 4:
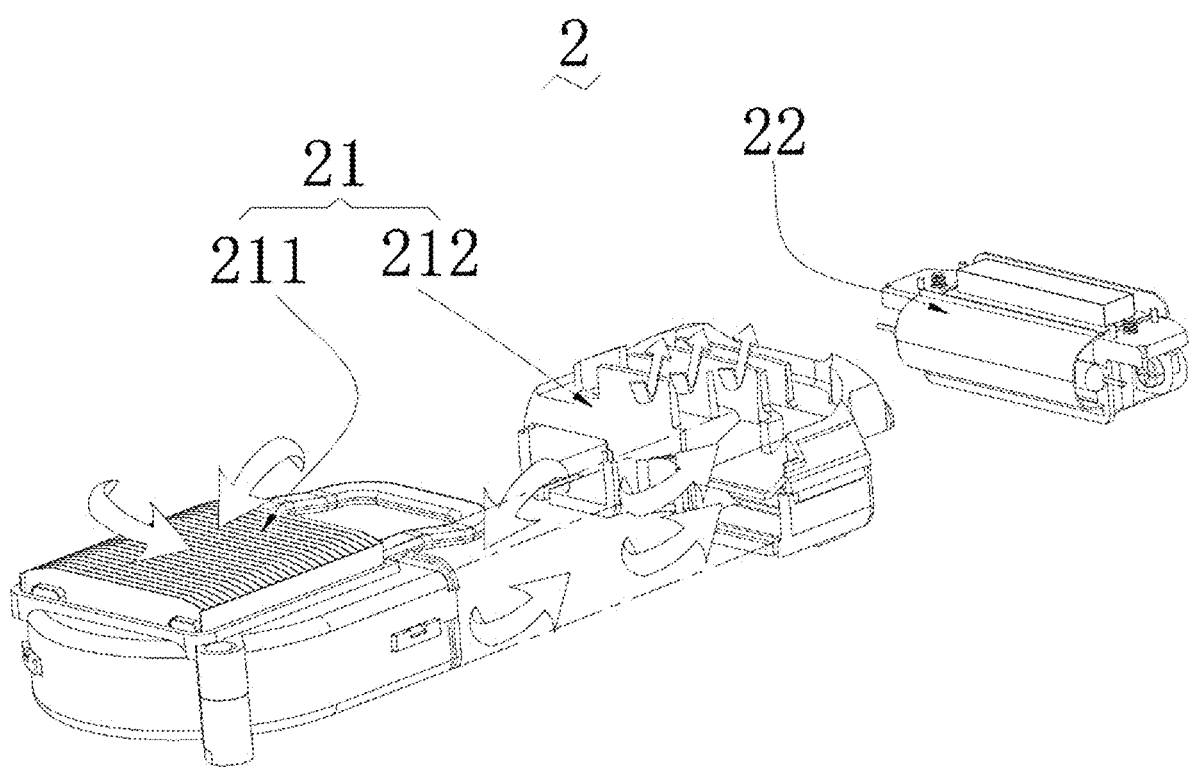
FIG. 4 is a second partial exploded view of a depilation apparatus in the portable depilation instrument according to the first embodiment of the present invention.

Referring to FIG. 4, the heat dissipation mechanism 21 includes a fan 211 and a heat conductive component 212. The fan 211 may be a centrifugal, axial-flow, mixed-flow, and cross-flow fan, or is optionally a centrifugal fan, so that external air mainly flows radially after axially entering an impeller of the fan. The heat conductive component 212 and the fan 211 may be connected through screw connection or clamping connection, so that air sucked by the fan 211 may flow through the heat conductive component 212 in a split direction. The depilation mechanism 22 is connected to one surface of the heat conductive component 212 away from the fan 211, and therefore, air flow in the heat conductive component 212 may perform cooling and temperature reduction on the demodulation mechanism 22, to achieve an ice compress effect on the human skin.

Figure 5:
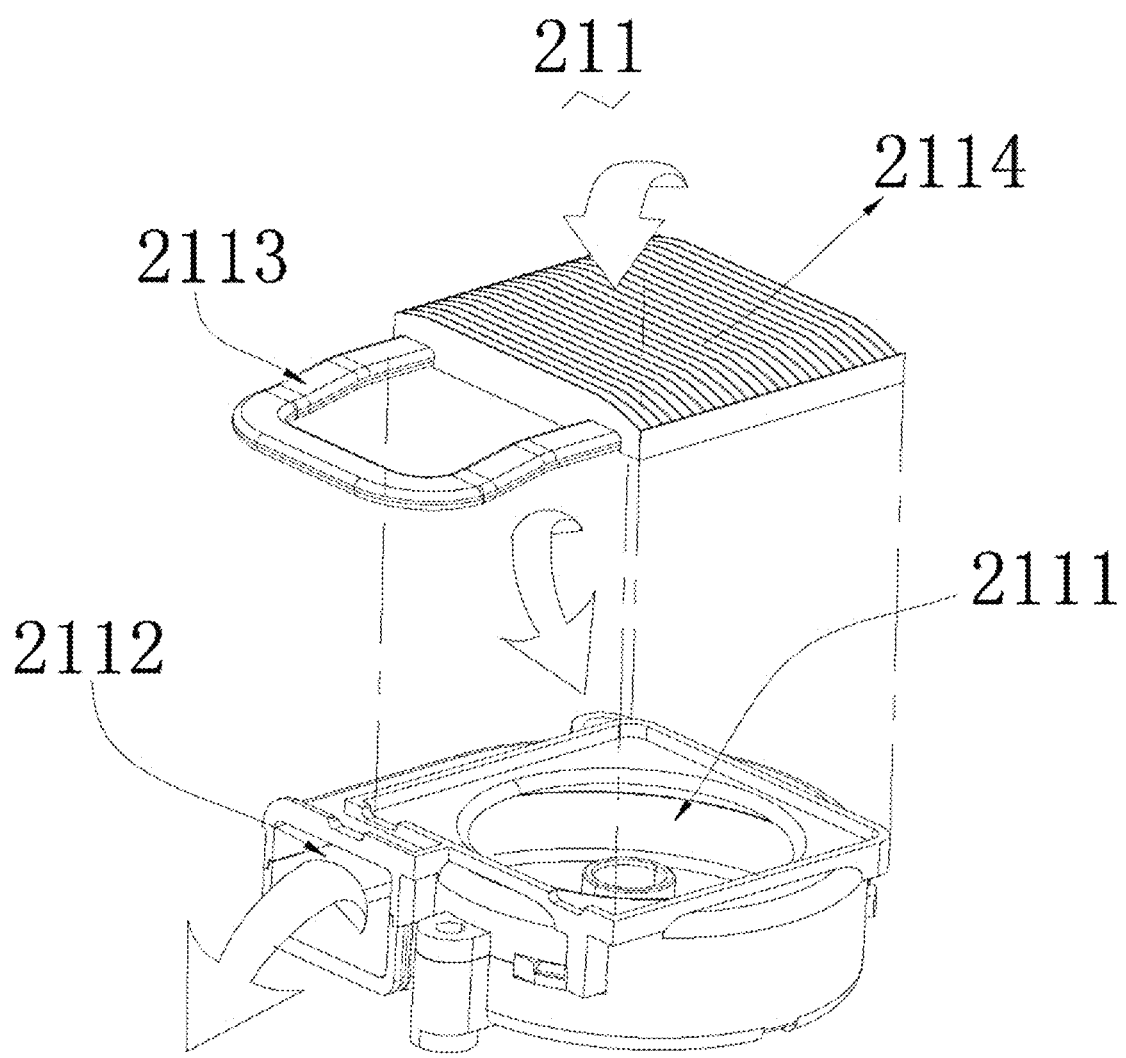
FIG. 5 is a first partial exploded view of a fan in the portable depilation instrument according to the first embodiment of the present invention.

Referring to FIG. 1 and FIG. 5, a specific structure of the fan 211 is as follows:

The fan 211 includes a fan air inlet 2111 and a fan air outlet 2112. A first heat dissipation fin 2114 is disposed at the fan air inlet 2111, and the first heat dissipation fin 2114 is disposed at an end portion of the heat conductive element 2113. That is, the heat conductive element 2113 is located at one end near the fan air inlet 2111, and the fan 211 is disposed at one end of the fan air inlet 2111 facing the inlet 11 on the shell 1, to suck air through inside of the inlet 11 on the shell 1, where the first heat dissipation fin 2114 completely covers the fan air inlet 2111, so that before entering the fan air inlet 2111, the external air passes through the first heat dissipation fin 2114 for heat dissipation and temperature reduction for a first time. A portion of the heat conductive element 2113 is inserted into the first heat dissipation fin 2114, and a remaining portion extends outward.

Further, the first heat dissipation fin 2114 may be a cast iron heat dissipation fin, a steel heat dissipation fin, and or an aluminum alloy heat dissipation fin. It may be understood that, because the first heat dissipation fin 2114 dissipates heat in the form of convection, a larger coverage area indicates a better heat dissipation effect.

Further, the heat conductive element 2113 may be a heat conductive tube, and a material of the heat conductive element is selected as a sheet structure or a tubular structure made of a metal or an alloy such as silver, copper, or iron, or is optionally a sheet structure. Due to a unique metal heat transfer property, the heat conductive element 2113 may dissipate the heat integrally through the first heat dissipation fin 2114.

It may be understood that, in actual production, the first heat dissipation fin 2114 and the heat conductive element 2113 are often of an integrated structure, and the first heat dissipation fin 2114 and the heat conductive element 2113 are connected together. Under the action of metal heat transfer, as the fan 211 sucks air inward, the heat on the heat conductive element 2113 flows quickly, thereby implementing quick temperature reduction.

Figure 6:
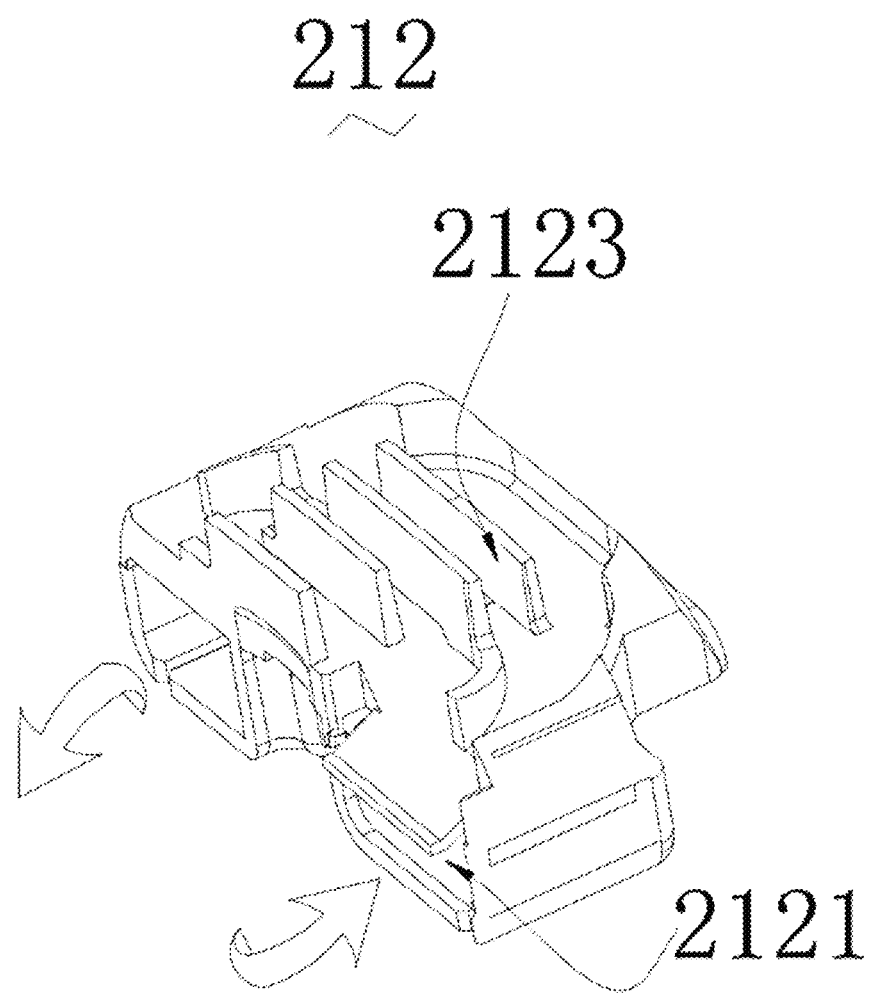
FIG. 6 is an exploded view of a heat conductive component in the portable depilation instrument according to the first embodiment of the present invention.

Referring to FIG. 6, the heat conductive component 212 includes a first vent 2121. The first vent 2121 is disposed at one end of the heat conductive component 212 facing the fan 211, or the first vent 2121 is optionally disposed parallel to one end of the heat conductive component 212, so that after entering through the first vent 2121 on one side, the external cooling medium is discharged in an opposite direction from the first vent 2121 on the other side. In addition, a second heat dissipation fin 2123 is disposed at a surface of one side of the heat conductive component 212, and the second heat dissipation fin 2123 is optionally disposed on an upper side of the heat conductive component 212.

Figure 7:
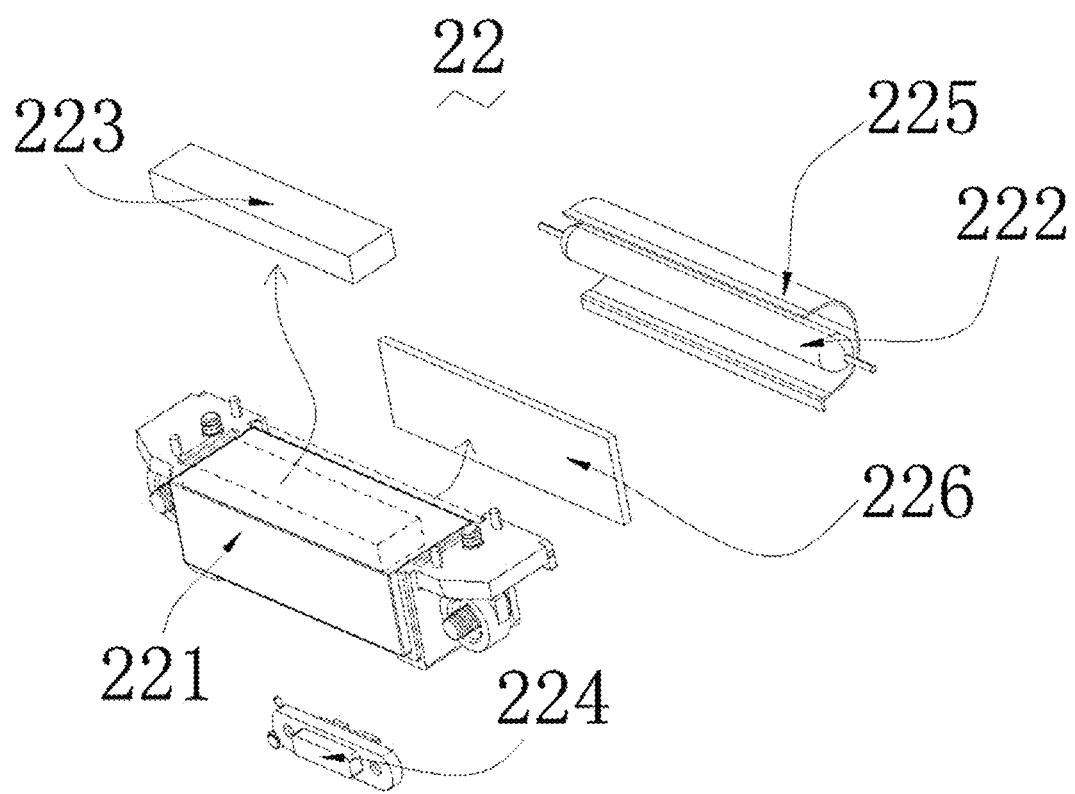
FIG. 7 is a first partial exploded view of a depilation mechanism in the portable depilation instrument according to the first embodiment of the present invention.

Referring to FIG. 7, the depilation mechanism 22 includes a cold compress portion 221, an emitter 222, a refrigeration element 223, a skin detection portion 224, a reflecting plate 225, an insulating plate 226, and a mounting component (not marked).

Both the emitter 222 and the refrigeration element 223 are electrically connected to the circuit apparatus 3, the cold compress portion 221 is clamped to the mounting component, the refrigeration element 223 is tightly attached to the cold compress portion 221 to cool the cold compress portion 221, the insulating plate 226 is located between the cold compress portion 221 and the emitter 222 to prevent heat of the emitter 222 from being transferred to the cold compress portion 221, and the reflecting plate 225 is disposed on one side of the emitter 222 away from the cold compress portion 221, so that light emitted by the emitter 222 is concentrated on the cold compress portion 221.

Further, the cold compress portion 221 is made of a crystal material, and specifically may be made of sapphire, K9 glass, or crystal glass, provided that a transparent crystal material is met. Optionally, the cold compress portion is made of a sapphire material.

It may be understood that, because the cold compress portion 221 is made of the sapphire, the cold compress portion 221 may be used as a light outlet. When the emitter 222 emits the light, because the sapphire has a relatively strong heat conductive property, the refrigeration element 223 and the cold compress portion 221 tightly attached to a surface of the emitter can efficiently generate a heat exchange, to achieve an optimal refrigeration effect. The cold compress portion 221 made of the sapphire may be round or rectangular, which is not limited herein. A surface of the cold compress portion 221 away from the emitter 222 is in contact with the human body, and a contact surface may be an arc surface or a flat surface, and is preferably a flat surface.

Further, the emitter 222 may be an IPL tube, and is located on one side of the cold compress portion 221 away from contact with the human body. The light emitted by the emitter 222 passes through the cold compress portion 221, and is emitted into skin of a user. A light color emitted by the emitter is not limited, the light may be a colored light, a composite light, or the like, and a specific wavelength and a frequency are determined according to a use situation.

Further, the skin detection portion 224 is electrically connected to the circuit apparatus 3 by using a capacitance touch detection principle. When the cold compress portion 221 is in contact with the skin, an internal preset capacitance detection apparatus detects whether a machine is actually in contact with the skin, to reduce a security problem caused by misoperations of the user.

Furthermore, a shape of the reflecting plate 225 is not limited, provided that the light from the emitter 222 is concentrated in a direction of the cold compress portion 221. The reflecting plate may be optionally U-shaped, an opening of the reflecting plate faces the cold compress portion 221, and the emitter 222 is located at a center of the opening of the U-shaped reflecting plate 225. In addition to concentrating the light, the reflecting plate also prevents a temperature of the emitter 222 during working from being dissipated to other places.

Figure 8:
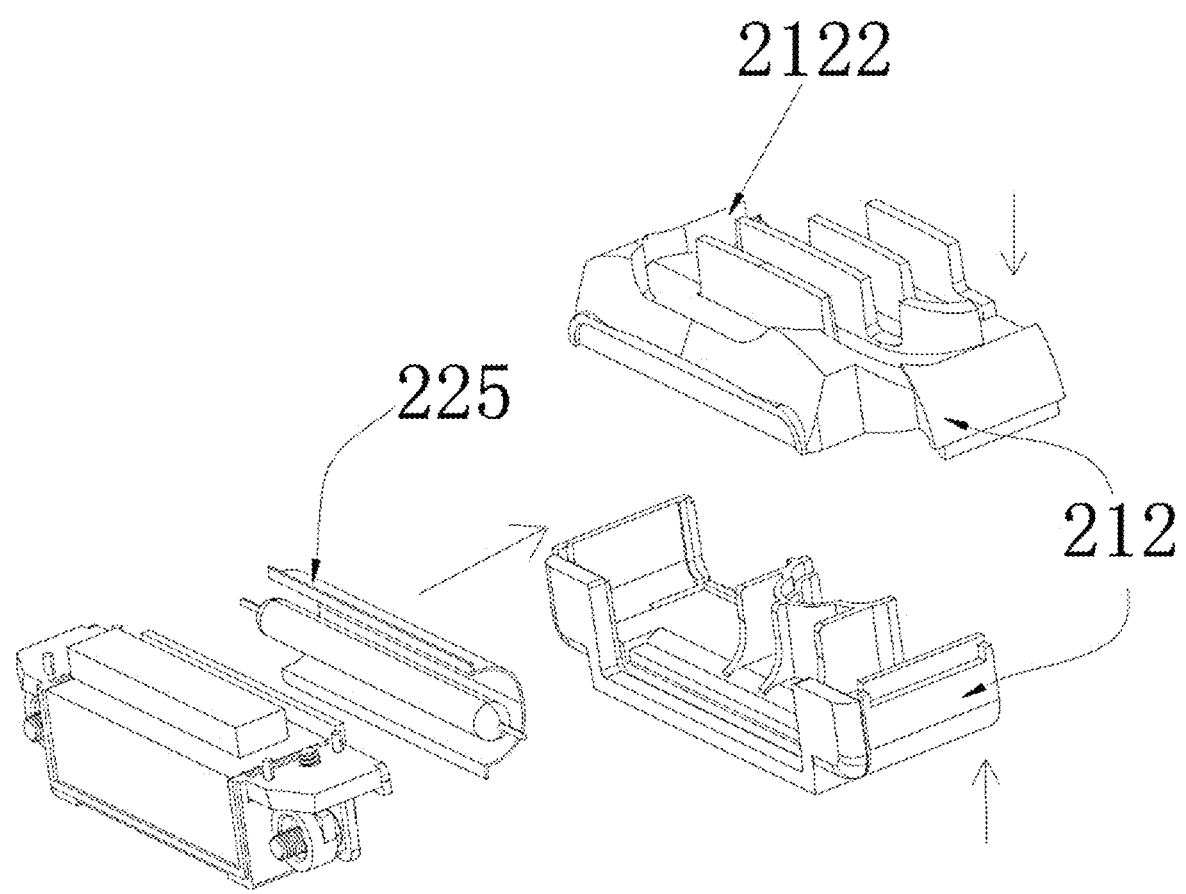
FIG. 8 is a third partial exploded view of the depilation apparatus in the portable depilation instrument according to the first embodiment of the present invention.

Referring to FIG. 8, the reflecting plate 225 is clamped to the heat conductive component 212, and is disposed on a surface away from the first vent 2121, so that the first vent 2121 forms a sealed channel.

Figure 9:
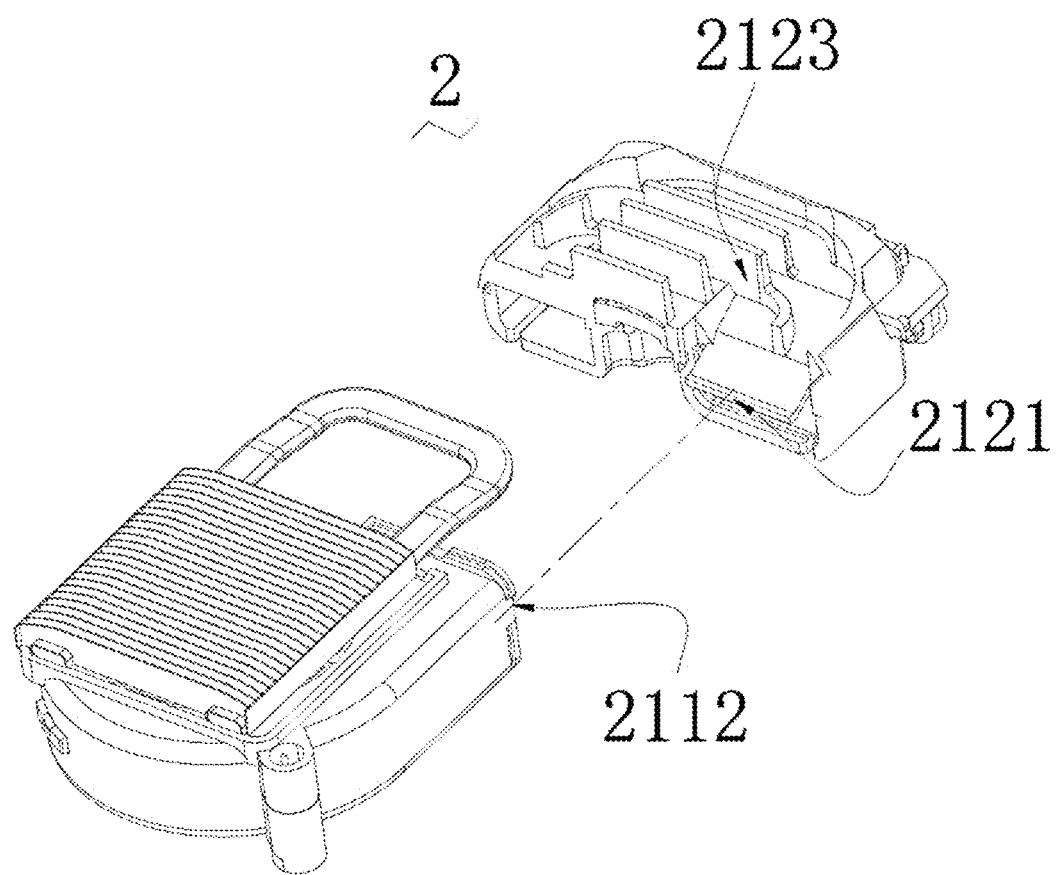
FIG. 9 is a second partial exploded view of the depilation mechanism in the portable depilation instrument according to the first embodiment of the present invention.
Figure 10:
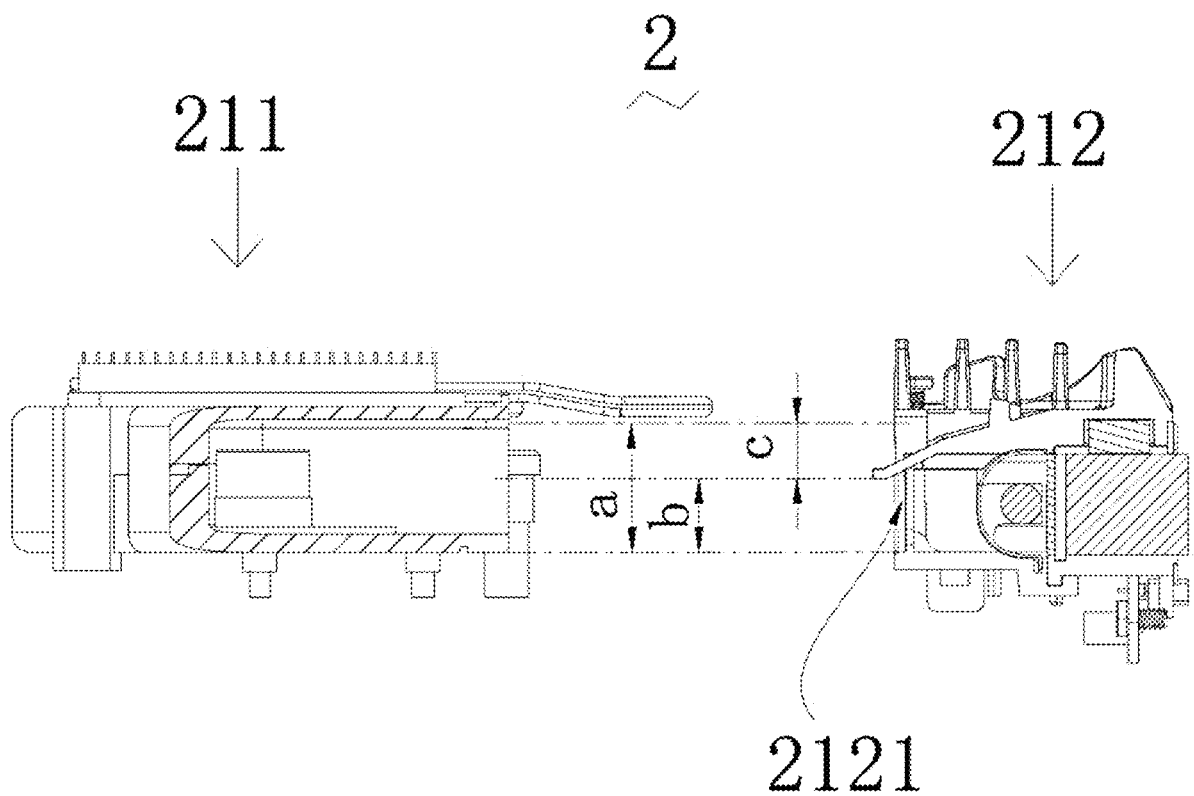
FIG. 10 is a cross-sectional view of the depilation mechanism in the portable depilation instrument according to the first embodiment of the present invention.

Referring to FIG. 8 and FIG. 9, when being connected, the fan 211 and the heat conductive component 212 are sleeved on the first vent 2121 through the fan air outlet 2112. Because a size a of the fan air outlet 2112 is greater than a size b of the first vent 2121, an extra gap c forms a second vent 2122, so that the air is divided into two directions in the first vent 2121 and the second vent 2122.

Figure 11:
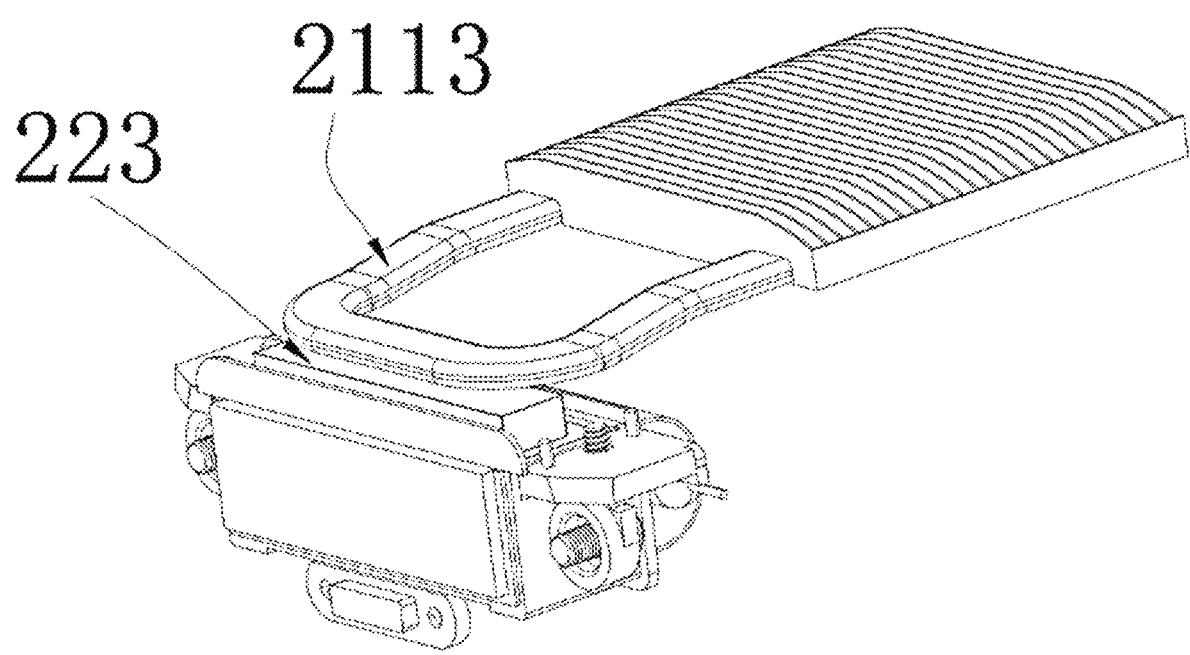
FIG. 11 is a fourth partial exploded view of the depilation apparatus in the portable depilation instrument according to the first embodiment of the present invention.
Figure 12:
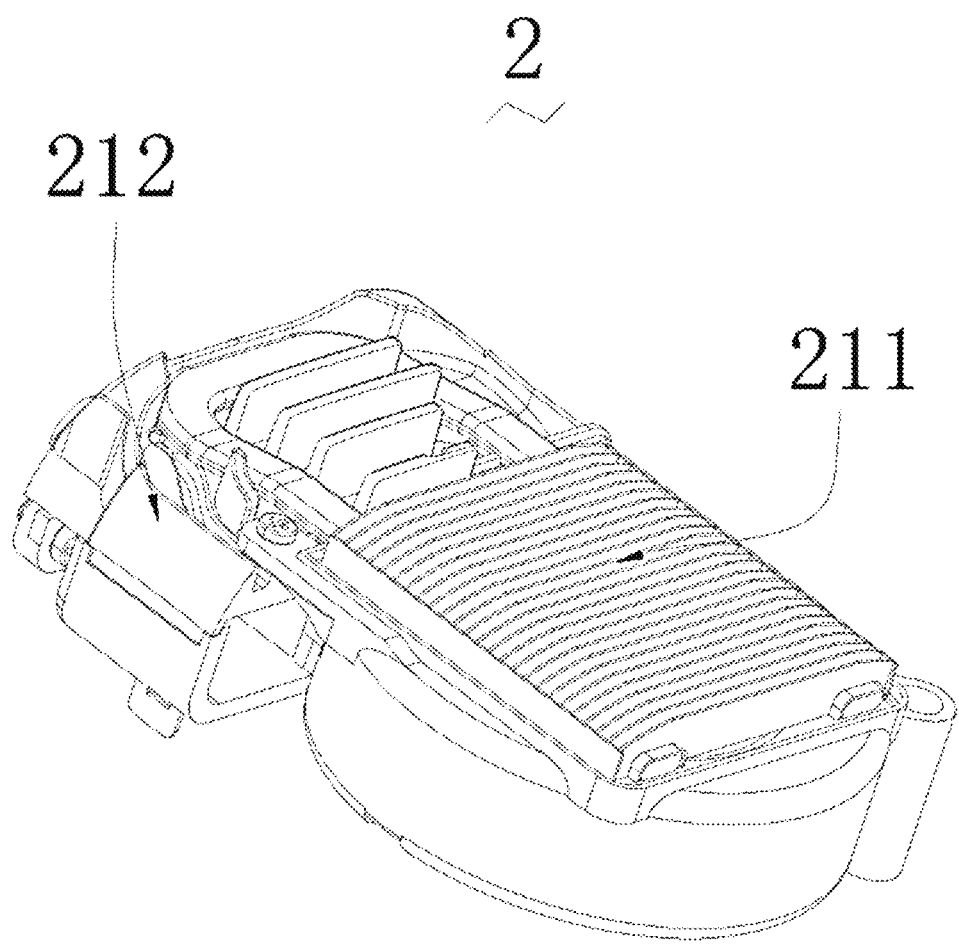
FIG. 12 is an assembled diagram of the depilation apparatus in the portable depilation instrument according to the first embodiment of the present invention.

Referring to FIG. 11 and FIG. 12, further, when the fan 211 and the heat conductive component 212 are connected, the heat conductive element 2113 on the fan 211 is tightly attached to the refrigeration element 223, and the first vent 2121 is exposed on one side of the fan 211, to discharge the air sucked by the fan 211.

Figure 13:
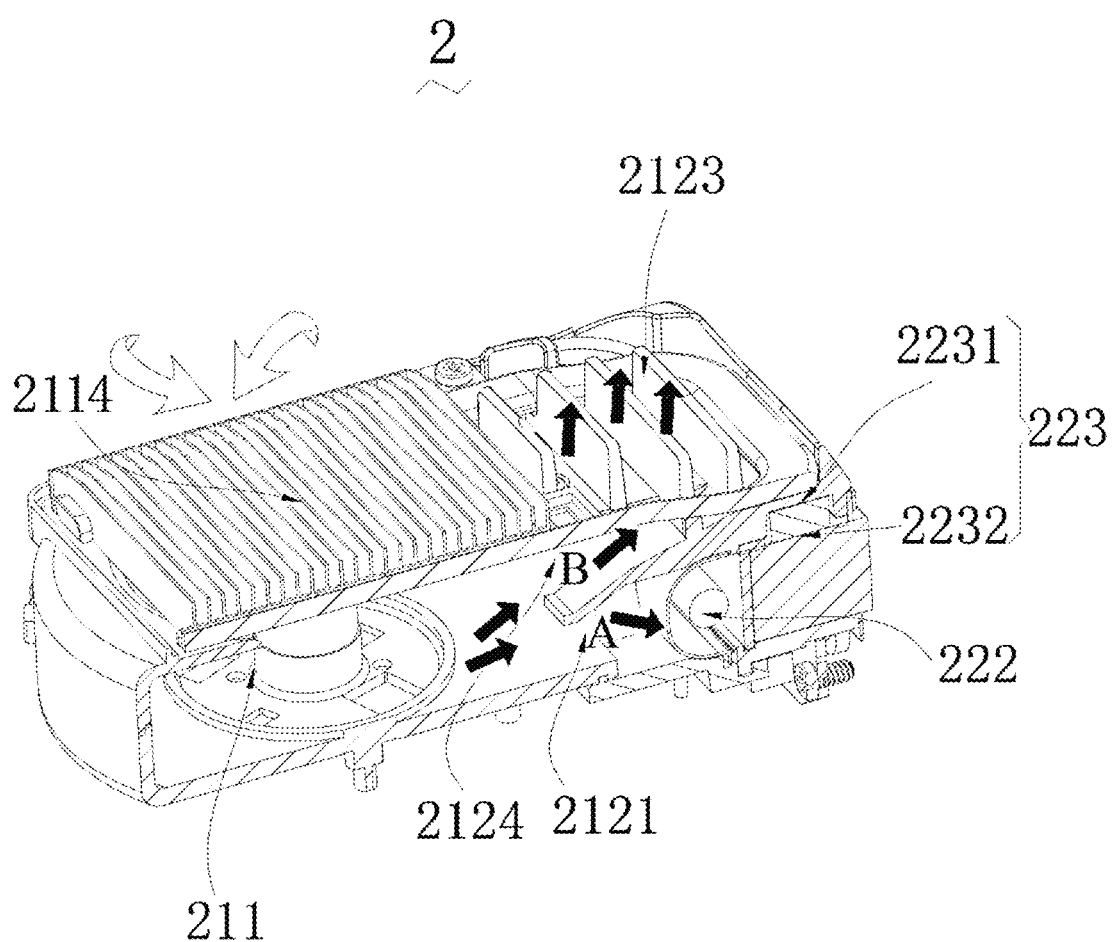
FIG. 13 is a cross-sectional view of the depilation apparatus in the portable depilation instrument according to the first embodiment of the present invention.

Referring to FIG. 11 and FIG. 13, the refrigeration element 223 is optionally a refrigeration element 223 in a semiconductor refrigeration manner, the refrigeration element 223 includes a heating surface 2231 and a refrigeration surface 2232 that are disposed opposite to each other, and the refrigeration surface 2232 of the refrigeration element 223 is tightly attached to the cold compress portion 221, to cool the cold compress portion 221.

It may be understood that, due to the particularity of the principle of the light depilation technology, a lot of heat is generated when the light is emitted, and when the cold compress portion 221 is in contact with the skin, to prevent the light from generating a burning pain to the user, a structure for temperature reduction needs to be disposed inside a body of the portable depilation instrument 100. Regardless of manners of temperature reduction, the heat is generated under the heat exchange, and the heating surface 2231 of the refrigeration element 223 is connected to the heat conductive element 2113. In addition to the refrigeration element 223, other internal elements, such as the emitter 222, and the power supply apparatus 4 and the circuit apparatus 3 inside the shell 1 all generate a lot of heat.

If the heat is not discharged in time, the refrigeration element 223 cannot achieve the refrigeration effect at maximum efficiency, thereby failing to reach a cooling temperature at which the skin is temporarily paralyzed.

Figure 14:
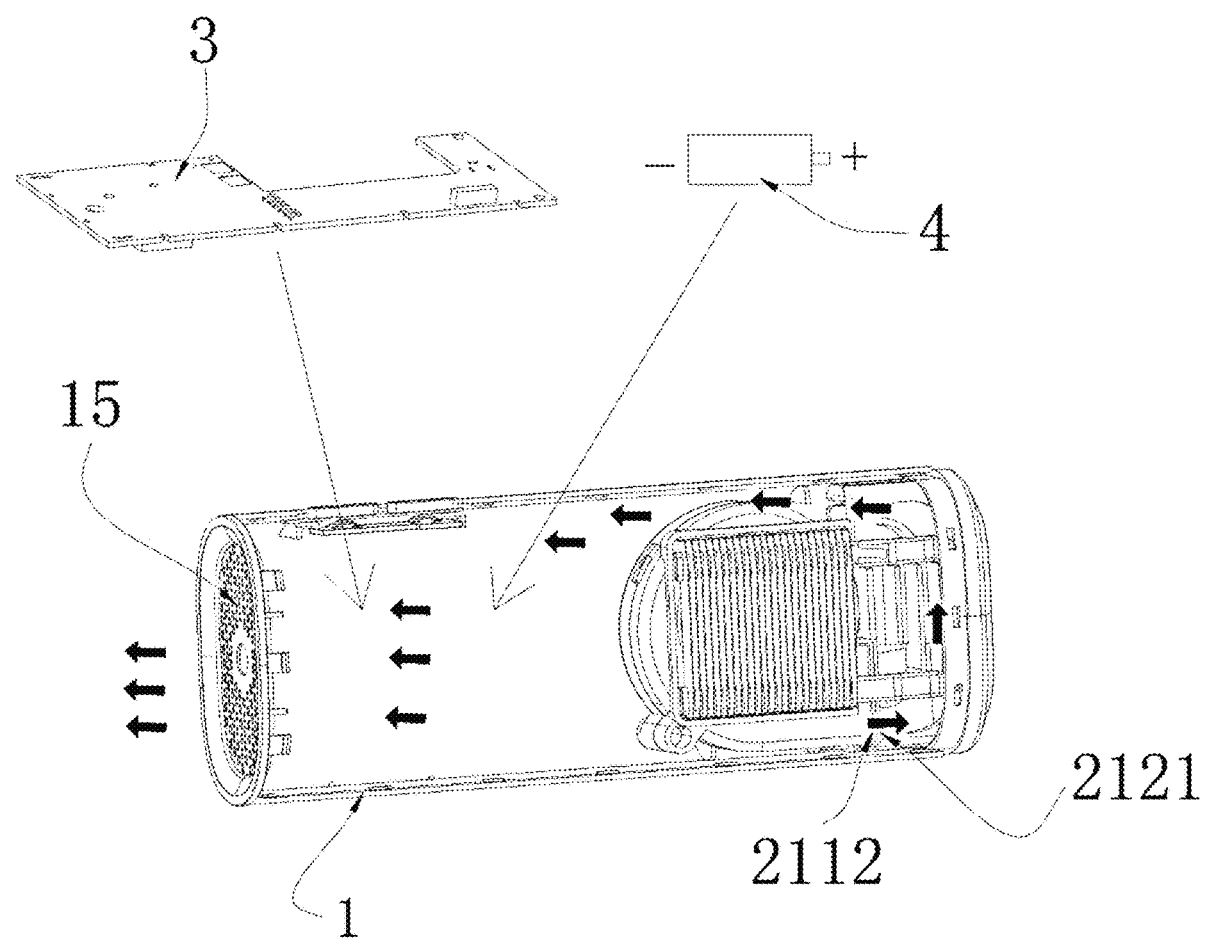
FIG. 14 is a partially omitted view of the portable depilation instrument according to the first embodiment of the present invention.
Figure 15:
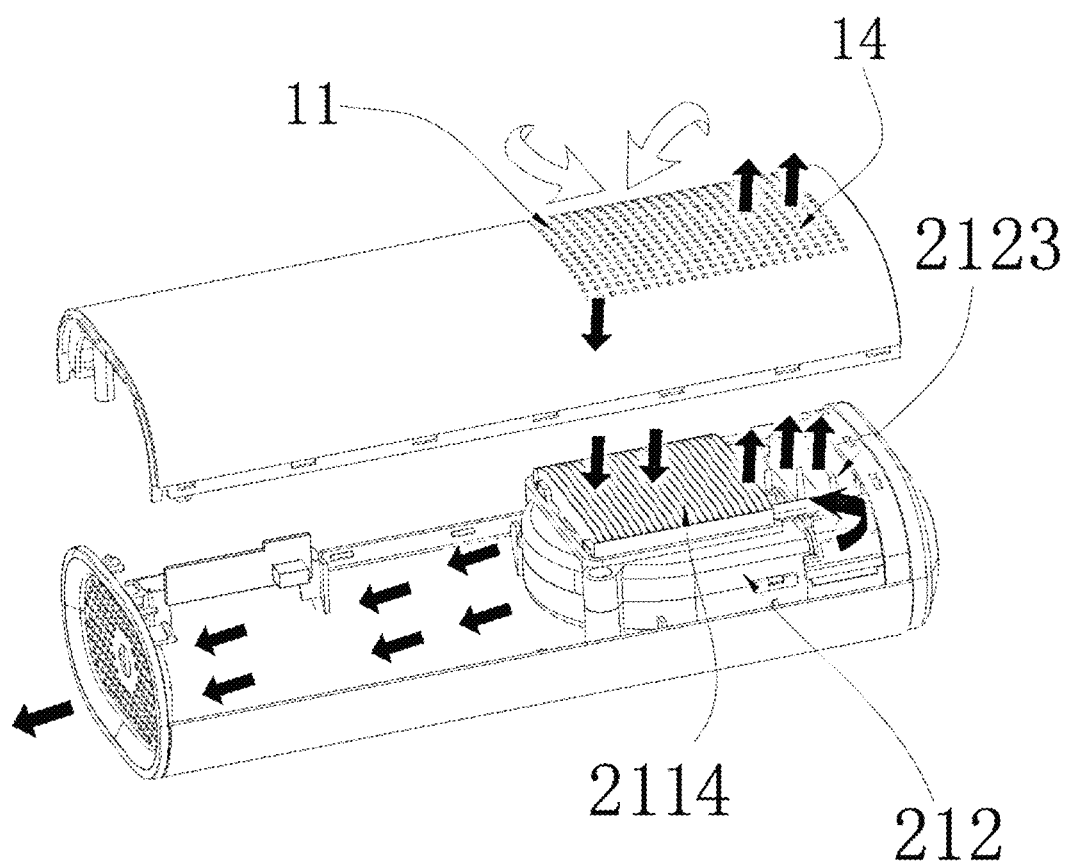
FIG. 15 is a partial exploded view of the portable depilation instrument according to the first embodiment of the present invention.

Referring to FIG. 13, FIG. 14, and FIG. 15, according to the foregoing two directions of the first vent 2121 and the second vent 2122 of the air, one of the directions is the first vent 2121, and the first vent 2121 is in communication with the first outlet 15 on the shell 1 to form a first channel A in which the air flows.

It may be understood that, the external air is sucked from the inlet 11. After entering the first vent 2121 through the second vent 2122, the external air passes through the emitter 222 to reduce a temperature of the emitter 222, then passes through the circuit apparatus 3 and the power supply apparatus 4 inside the shell 1, and is discharged from the first outlet 15 of the shell 1, to form an air path of the first channel, and temperature reduction and cooling are also performed on regions through which the air passes. For example, the circuit apparatus 3 and the power supply apparatus 4 are disposed in the region through which the air passes, that is, one side of inside of the shell 1 near the first outlet 15, to perform heat dissipation on the circuit apparatus 3 and the power supply apparatus 4 and bring the air out of the first outlet 15.

The heat conductive component 212 and the second heat dissipation fin 2123 at an upper end of the heat conductive component are integrated, an outer surface of the heat conductive component 212 and an inner wall of the shell 1 are enclosed to form a space, and a second vent 2122 is formed at the fan air inlet 2111 in an attachment manner. The second heat dissipation fin 2123 is disposed in the space and faces the second outlet 14, so that the air exits in a direction towards the second outlet 14, and therefore, the second vent 2122 and the second outlet 14 on the shell 1 form a second channel B.

It may be understood that, the second heat dissipation fin 2123 not only has a function of heat dissipation, but also has a function of guiding the air. Based on this, the second heat dissipation fin is designed as a fin structure, so that internal air may directly exit towards the second outlet 14. When passing through the second heat dissipation fin 2123, the air flows at the refrigeration element 223, to perform temperature reduction on the refrigeration element 223. The reason why the air is directly discharged is that the refrigeration element 223 is an element that generates a maximum amount of heat inside the portable depilation instrument 100, and therefore a path of the air in an air circulation needs to be reduced, so that the air is discharged at the first time, thereby achieving the cooling and temperature reduction effect at maximum efficiency.

Based on the first channel A and the second channel B, in some embodiments, a manner of heat dissipation is not using the fan 211 for air cooling, but an external cooling medium such as water or coolant may be used, provided that the external medium can bring heat of the two channels.

Based on the first channel A and the second channel B, in some embodiments, the heat dissipation mechanism 21 may not have the heat conductive element 2113 and the first heat dissipation fin 2114, and may perform heat dissipation on the emitter 222 and the refrigeration element 223 by directly using air of the fan 211 or another medium.

The second outlet 14 is disposed on one side of the inlet 11, both are disposed on a side surface of the shell 1 near one end of the heat conductive element 2113, and the first outlet 15 is located at an end portion of the shell 1 away from the heat conductive element 2113, so that air of the first channel is able to completely pass through inside of the entire shell 1, and an air inlet direction of the inlet 11 is parallel to an air outlet direction of the second outlet 14, and is perpendicular to an air outlet direction of the first outlet 15.

A contact end surface between the cold compress portion 221 and the skin is disposed on a same side as an end surface at which the skin detection portion 224 is exposed, so that when light depilation is performed on the skin, the cold compress portion 221 is in contact with a periphery of the irradiated skin, to perform cold compress and temperature reduction on the periphery of the irradiated skin, to reduce a burning sensation generated by the irradiated skin. In addition, the cold compress portion 221 may be close to zero temperature, to really make the skin near the light outlet reach infinitely close to a freezing point, so that the burning sensation of the skin can be alleviated, and short-time contact does not cause skin damage.

Under the guidance of the second heat dissipation fin 2123, air entering the second vent 2122 is directly discharged from the first outlet 15 after passing through the heat conductive element 2113. In this way, an air path of the second channel is formed, and similarly, temperature reduction and cooling are performed on the regions through which the air passes.

In the present invention, an improvement is made on a portable depilation instrument using an original heat dissipation mode. The fan 211 is used to suck external air, through the heat conductive component 212, an air direction separately flows to the first channel and the second channel, the first channel and the second channel are completely isolated, the refrigeration element 223 and the emitter 222 are respectively located in positions through which the first channel and the second channel pass, and as the air flows in the completely isolated first channel and second channel, heat dissipation is separately performed on the refrigeration element and the emitter; and the first channel may further perform temperature reduction on other heat generation elements inside the shell 1, for example, elements such as the circuit apparatus 3 and the power supply apparatus 4, to achieve an efficient and complete temperature reduction and cooling effect.

In some embodiments, a plurality of channels more than the two channels in this embodiment are provided. Except the refrigeration element 223 and the emitter 222, a plurality of channels may be alternatively provided, and other heat generation elements are alternatively disposed in remaining channels. This falls within the protection scope of the present invention.

In some embodiments, a portable depilation instrument is provided with a light-emitting body (not shown in the figure), and structural features described in all the foregoing embodiments are used.

Embodiment 2

To better resolve the foregoing problem of incomplete heat dissipation, the present invention further provides a second embodiment. The second embodiment is an extension on the basis of the portable depilation instrument 100 in the first embodiment, and includes all features of the portable depilation instrument 100 in the first embodiment.

Figure 16:
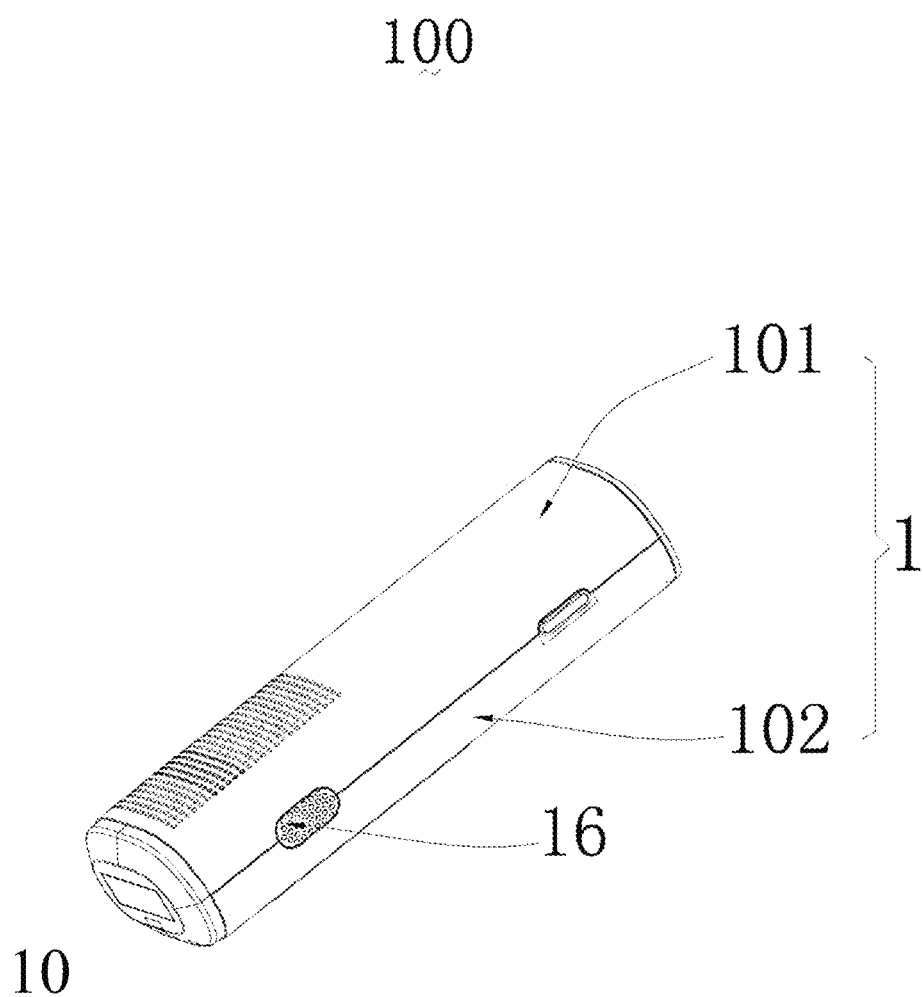
FIG. 16 is a schematic structural diagram of a portable depilation instrument according to a second embodiment of the present invention.
Figure 17:
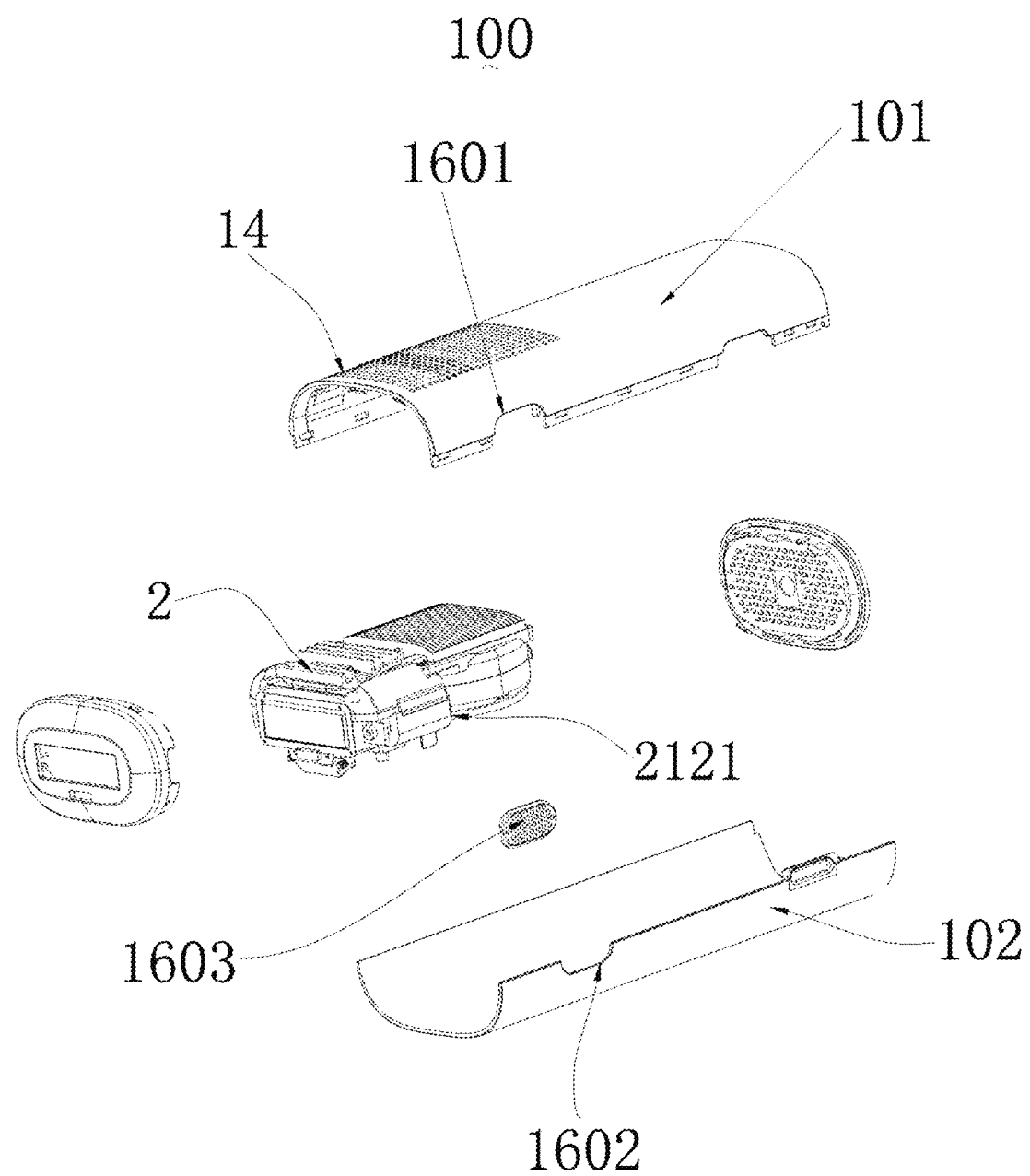
FIG. 17 is an expanded view of a part structure of the portable depilation instrument according to the second embodiment of the present invention.

Referring to FIG. 16 and FIG. 17, the portable depilation instrument 100 provided in the second embodiment is provided with a third outlet 16 on the shell 1, and the third outlet 16 is optionally disposed on a peripheral side of the first vent 2121, and is in communication with a cavity inside the shell 1, so that the external cooling medium from the first vent 2121 may be discharged from the third outlet 16 on the peripheral side of the shell 1.

Further, in the present invention, optionally, the upper shell 101 and the lower shell 102 are respectively disposed on a first groove 1601 and a second groove 1602, an exhaust structure 1603 capable of being in communication with the inside of the shell 1 is disposed between the first groove 1601 and the second groove 1602, and after the upper shell 101 and the lower shell 102 are connected, a gap is formed between the first groove 1601 and the second groove 1602, and the exhaust structure 1603 is disposed in the gap to cause the cavity inside the shell 1 to be in communication with outside, to form a third outlet 16.

Figure 18:
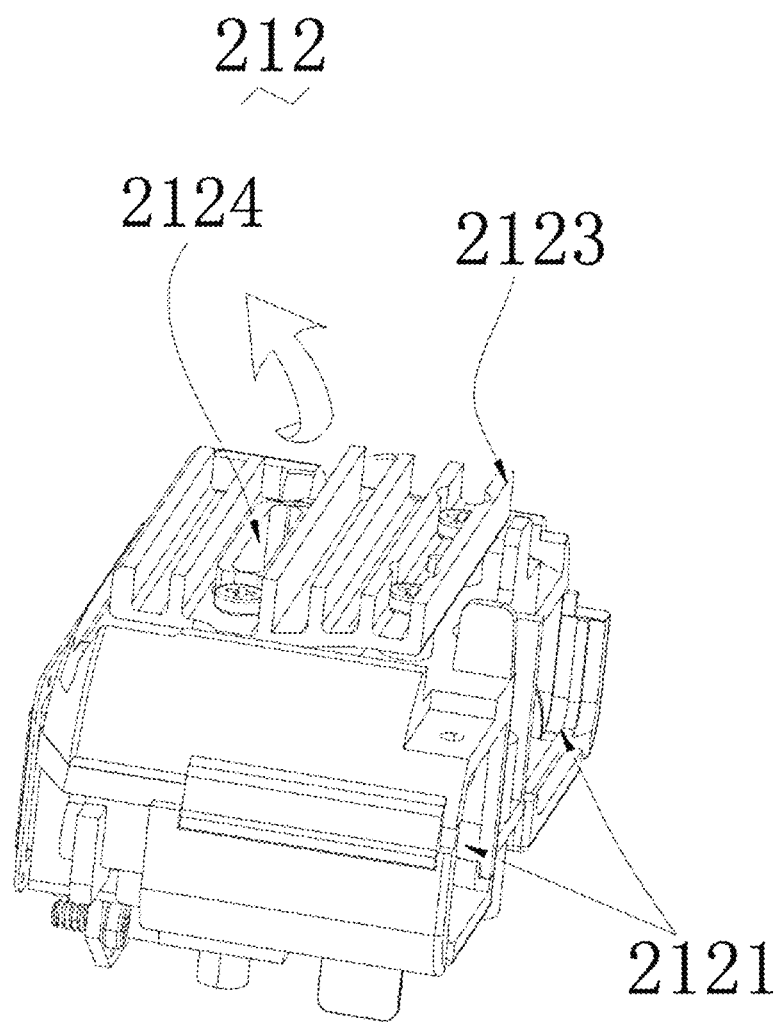
FIG. 18 is a schematic structural diagram of a heat conductive component in the portable depilation instrument according to the second embodiment of the present invention.
Figure 19:
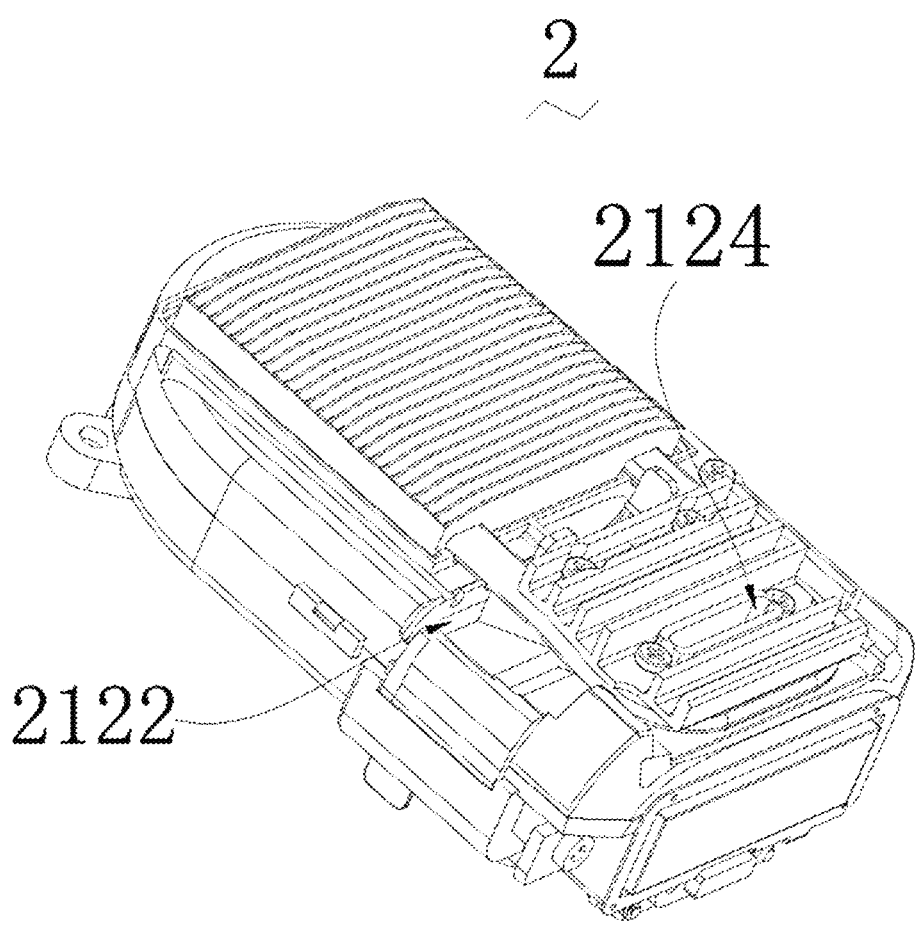
FIG. 19 is a schematic structural diagram of a depilation apparatus in the portable depilation instrument according to the second embodiment of the present invention.

Referring to FIG. 18 and FIG. 19, furthermore, the heat conductive component 212 is provided with a third vent 2124 at the second heat dissipation fin 2123, the third vent 2124 faces a guiding direction of the second heat dissipation fin 2123, that is, faces a direction of the second outlet 14, and the third vent 2124 is in communication with the first vent 2121, so that the external cooling medium is discharged through the third vent 2124 in a direction from the second heat dissipation fin 2123 to the second outlet 14 after passing through the first vent 2121, to better speed up a progress of the heat exchange, thereby achieving a better cooling effect on the depilation mechanism 2.

The third vent 2124 is only a means of implementing the communication of the first vent 2121, and a quantity and a communication manner are not limited. That is, a fourth or fifth vent may be alternatively provided, or the heat conductive component 212 is correspondingly provided with at least three through holes provided on a surface of the second heat dissipation fin 2123, so that the vent is in communication with the first vent 2121, provided that the external cooling medium that flows inside the first vent 2121 is discharged through the second heat dissipation fin 2123.

Therefore, through the first vent 2121 and the second vent 2122, and under the action of the first outlet, the second outlet, the third outlet (not shown in the figure), the first vent 21, the second vent 2122, and the third vent 2124, the cooling efficiency is further improved, so that better ice feeling experience is brought to the user.

As summarized in Embodiment 2, the outlets disposed on the shell 1 and the vents on the depilation mechanism 2 are mainly described in this embodiment. Both a quantity of the outlets and a quantity of the vents are not limited. For example, the third outlet 16 is mainly used for discharging the external cooling medium passing through the first vent 2121 to the outside of the shell 1, or the third vent 2124 is mainly used for discharging the external cooling medium passing through the first vent 2121 to the outside of the shell 1 through the second heat dissipation fin 2123.

A person skilled in the art should also understand that if all or a part of the components of the structure in the present invention are combined in a manner of fusion, physical connection, or the like, for example, positions of the components in the depilation apparatus 2 are moved; or the components are integrated; or the components are detachably designed; and a replacement of a feature quantity and a change in feature morphology that is not used as a function are made, all combined components may form a device/apparatus with a specific function, and such a device/apparatus replaces a corresponding component in the present invention, and also falls within the protection scope of the present invention.

Compared with the prior art, the portable depilation instrument provided in the present invention has the following advantages. To help users hold, all the household portable depilation instruments are designed relatively small. Therefore, due to accumulation of a large amount of heat, heat dissipation is a very important problem, and if the heat dissipation is not good, a pain may be brought to the users during depilation, and even a security problem is caused. Previously, only a single inlet and a single outlet are provided in the portable depilation instrument, to form a channel for heat dissipation. However, it is not only a single element that generates heat inside the portable depilation instrument. However, if a plurality of heat generation elements rely on a single channel formed by one inlet and one outlet for heat dissipation, heat generated by the heat generation elements affect each other, resulting in a poor heat dissipation effect, and a working environment of the heat generation elements in the channel is affected. For example, the refrigeration element and the emitter that both generate heat are placed in a same heat dissipation channel. When passing through one of the refrigeration element and the emitter, the external cooling medium brings the heat to another place. Therefore, in the present invention, a plurality of heat dissipation channels are provided in the portable depilation instrument, and different heat generation elements may be disposed in different heat dissipation channels. The heat dissipation channel may be one inlet corresponding to a plurality of outlets, or may be a plurality of inlets corresponding to one outlet. Therefore, under the action of the heat conductive component, the external cooling medium may cool a plurality of heat generation elements inside the shell of the portable depilation instrument without interfering with each other.

The foregoing descriptions are only preferred embodiments of the present invention, but are not intended to limit the present invention. Any modification, equivalent replacement, or improvement made without departing from the principle of the present invention shall fall within the protection scope of the present disclosure.

What is claimed is:

1. A portable depilation instrument, comprising:
a shell, and a depilation mechanism and a heat dissipation mechanism inside the shell,
wherein the shell is provided with at least two outlets and one inlet;
the heat dissipation mechanism comprises a heat conductive component; and
the one inlet is separately in communication with different outlets of the at least two outlets, to form at least two channels; each of the at least two channels is provided with an element generating heat; and the heat conductive component is configured to guide an external cooling medium introduced from the one inlet to separately pass through different channels of the at least two channels and the external cooling medium is then discharged from a corresponding outlet of the at least two outlets, allowing heat of the at least two channels to be discharged out of the shell;
wherein the external cooling medium is air, a fan is provided inside the shell, the fan is provided with a fan air inlet, and the fan is disposed such that one side of the fan air inlet of the fan faces the one inlet on the shell, to suck the air into an inside of the shell; and
the heat dissipation mechanism further comprises a heat conductive element, a first portion of the heat conductive element is disposed between the fan air inlet of the fan and the one inlet, the air is introduced from the one inlet on the shell, the first portion of the heat conductive element is provided with a first heat dissipation fin, and a second portion of the heat conductive element extends to a refrigeration element.

2. The portable depilation instrument according to claim 1, wherein the at least two outlets comprise a first outlet and a second outlet, an outer surface of the heat conductive component is provided with a second heat dissipation fin, and the heat conductive component is provided with a first vent and a second vent;
the one inlet, the first vent, and the first outlet are sequentially in communication with each other to form a first channel of the at least two channels; and
the one inlet, the second vent, and the second outlet are sequentially in communication with each other to form a second channel of the at least two channels.

3. The portable depilation instrument according to claim 2, wherein the at least two outlets further comprise a third outlet, and the third outlet is in communication with an internal cavity of the shell.

4. The portable depilation instrument according to claim 3, wherein the third outlet is disposed on a side surface or one side facing away from the second outlet of the shell.

5. The portable depilation instrument according to claim 4, wherein the shell comprises an upper shell and a lower shell, the upper shell and the lower shell are respectively provided with a first groove and a second groove, an exhaust structure configured to be in communication with an inside of the shell is disposed between the first groove and the second groove, and after the upper shell and the lower shell are connected, a gap is formed between the first groove and the second groove, and the exhaust structure is disposed in the gap to cause the internal cavity of the shell to be in communication with an outside, to form the third outlet.

6. The portable depilation instrument according to claim 2, wherein the heat conductive component is provided with a third vent at the second heat dissipation fin, the third vent faces a guiding direction of the second heat dissipation fin, and the third vent is in communication with the first vent.

7. The portable depilation instrument according to claim 6, wherein the third vent is disposed between the first vent and the second outlet.

8. The portable depilation instrument according to claim 2, wherein the external cooling medium is air, the depilation mechanism comprises a refrigeration element and an emitter, the refrigeration element is located in a first region, wherein the second channel passes through the first region, and the emitter is located in a second region, wherein the first channel passes through the second region.

9. The portable depilation instrument according to claim 1, wherein the second outlet is disposed on one side of the one inlet, the second outlet and the one inlet are disposed on a side surface of the shell near one end of the heat conductive element, and the first outlet is located at an end portion of the shell away from the heat conductive element, so that air of the first channel completely passes through an inside of the shell, and simultaneously takes the heat inside the shell out, and an air inlet direction of the one inlet is parallel to an air outlet direction of the second outlet, and the air inlet direction of the one inlet is perpendicular to an air outlet direction of the first outlet.

10. The portable depilation instrument according to claim 1, wherein the depilation mechanism further comprises a cold compress portion, and the shell comprises a holding portion and a head portion, wherein the head portion is provided with an opening throughout the head portion, and a portion of the cold compress portion passes through the opening, and the portion of the cold compress portion is exposed on a surface of the shell, to be in contact with a human skin.

11. The portable depilation instrument according to claim 10, wherein the cold compress portion is made of a crystal material, and the emitter is also disposed inside the opening, and the emitter is located on one side of the cold compress portion away from contact with a human body, so that a light emitted by the emitter passes through the cold compress portion, to be emitted into a skin of a user.

12. The portable depilation instrument according to claim 10, further comprising: a circuit apparatus and a power supply apparatus, wherein the circuit apparatus and the power supply apparatus are located inside the shell, and the circuit apparatus and the power supply apparatus are located in the second region, the circuit apparatus and the power supply apparatus are electrically connected to the refrigeration element, the refrigeration element is a semiconductor refrigeration element, the refrigeration element comprises a refrigeration surface and a heating surface, wherein the refrigeration surface and the heating surface are disposed opposite to each other, and the refrigeration surface of the refrigeration element is tightly attached to the cold compress portion, to cool the cold compress portion; and the heating surface of the refrigeration element is connected to a heat conductive element, to dissipate the heat and also cool the cold compress portion.

13. The portable depilation instrument according to claim 12, further comprising: a skin detection part, electrically connected to the circuit apparatus.

14. The portable depilation instrument according to claim 10, wherein the depilation mechanism further comprises a reflecting plate disposed on one side of the emitter away from the cold compress portion.

15. The portable depilation instrument according to claim 14, wherein the reflecting plate is clamped to a side of the heat conductive component away from the first vent.

16. The portable depilation instrument according to claim 1, wherein the first heat dissipation fin is disposed between the one inlet and the fan air inlet.

17. The portable depilation instrument according to claim 1, wherein the heat conductive element is a heat conductive tube.

18. The portable depilation instrument according to claim 1, wherein the first vent is disposed at one end of the heat conductive component facing the fan.

19. The portable depilation instrument according to claim 18, wherein the fan is further provided with a fan air outlet sleeved on the first vent.

20. The portable depilation instrument according to claim 19, wherein a size of the fan air outlet is greater than a size of the first vent.

* * * * *